United States Patent [19]

McDonald

[11] Patent Number: 5,128,449
[45] Date of Patent: Jul. 7, 1992

[54] POLYPEPTIDE AND A METHOD FOR ITS PRODUCTION

[75] Inventor: Ted P. McDonald, Knoxville, Tenn.

[73] Assignee: The University of Tennessee Research Corporation, Knoxville, Tenn.

[21] Appl. No.: 215,071

[22] Filed: Jul. 5, 1988

[51] Int. Cl.[5] .......................................... C07K 15/14
[52] U.S. Cl. .................................. 530/351; 530/395; 530/350; 530/397
[58] Field of Search ................ 530/350, 395, 351, 397

[56] References Cited

PUBLICATIONS

Abstract, Dialog File 155, Accession No. 87060550 of de Moreno et al. 1986. J. Pharm. Sci 75(9): 907-911.
Chemical Abstracts no. 104: 3023m of Compton et al. 1985. Anal. Biochem 151(2): 369-374.
Arthur, G. et al. 1984. Can. J. Biochem. Cell. Biol. 62(11): 1059-1063 (abstract).
Casazza, A. M. et al. 1978. Tumori 64(2): 115-130 (abstract).
Krystal, G. et al. 1986. Blood 67(1): 71-79.
Suncereau-Dassin, et al. 1985. Haemortaser 15: 182-188.
Tayrien, G. et al. 1987. J. Biol. Chem. 262(7): pp. 3262-3268.
T. P. McDonald et al, Studies on the Purification of Thombopoietin from Kidney Cell Cultrure Medium, pp. 162-174, Aug. 1985.
Journal of Laboratory and Clinical Medicine, vol. 106, No. 2.
T. P. McDonald, Thrombopoietin: Its Biology, Purification, and Characterization, Experimental Hematology-16:201-205 (1988).
G. D. Kalmaz and T. P. McDonald, Assay for Thrombopoietin: A New, More Sensitive Method Based on Measurement of the Small Acetycholinesterase-Positive Cell (41421)-Proceedings of Soc. for Exp. Biology and Medicine 170, pp. 213-219 (1982).
T. P. McDonald, A Comparison of Platelet Size, Platelet Count, and Platelet 35S Incorporation as Assays for Thrombopoietin British Journal of Haematology, 1976, 34, 257.

Ted P. McDonald, Assays for Thrombopoietin Scand J. Haematol (1977) 18, pp. 5-12.
T. P. McDonald, et al, A Comparison of Mice in Rebound-Thrombocytosis with Platelet-Hypertransfused Mice for the Assay of Thrombopoietin Scand J Haematol (1976) 16, 326-334.
T. P. McDonald, et al, Thrombopoietin Production by Human Embryonic Kidney Cells in Culture, Reprint from the Journal of Laboratory and Clinical Medicine, St. Louis, vol. 85, No. 1, pp. 59-66, Jan., 1975.
T. P. McDonald et al, Immunologic Similarities of Thrombopoietin from Different Sources Scand J Haematol (1977) 18, pp. 91-97.
T. P. McDonald, Effects of Different Route Administration and Injection Schedules of Thrombopoietin on 35S Incorporation into Platelets of Assay Mice (39732)1-Proceedings of the Soc. for Experimental Biology and Medicine 155, pp. 4-7 (1977).
T. P. McDonald et al, Assay for Thrombopoietin: A Comparison of Time of Isotope Incorporation into Platelets and the Effects of Different Strains and Sexes of Mice[1], Exp. Hemat., Jul., 1979, MN 496, vol. 7, No. 6, pp. 289-296.

(List continued on next page.)

Primary Examiner—Margaret Moskowitz
Assistant Examiner—Keith C. Furman
Attorney, Agent, or Firm—Luedeka, Hodges, Neely, & Graham

[57] ABSTRACT

The present invention provides for a new polypeptide and a method for producing the same. The polypeptide has a molecular weight of approximately 30,000 daltons as a dimer and a monomer molecular weight of about 15,000 daltons, an isoelectric pH of about 4.47 and an activity of at least 21,000 units per milligram of protein in the monomer or dimer state. The preferred method comprises chromatographing a crude polypeptide-containing medium on a dextran derived chromatography column; precipitating the eluate in a water-ethanol solution; electrophoresing the precipitate in a polyacrylamide gel; and chromatographing the extract on a reverse phase-high performance liquid chromatography column.

1 Claim, 11 Drawing Sheets

OTHER PUBLICATIONS

T. P. McDonald and Chris Nolan, Partial Purification of a Thrombocytopoietic Stimulating Factor from Kidney Cell Culture Medium, Biochemical Medicine 21, pp. 146–155 (1979).

T. P. McDonald and Rose Clift, Effects of Thrombopoietin and Erthropoietin on Platelet Production in Rebound-Thrombocytotic and Normal Mice, American Home Journal of Hematology 6:219–228 (1979).

T. P. McDonald, Effect of Thrombopoietin on Platelet Size of Mice Exp. Hema., May, 1980, vol. 8, No. 5, pp. 527–532.

T. P. McDonald et al, Characterization of a Thrombocytopoietic-Stimulating Factor from Kidney Cell Culture MEdium, Exp. Hematol, Mar. 1981, vol. 9, No. 3, pp. 288–296.

G. D. Kalmaz[1] and T. P. McDonald, Effects of Antiplatelet Serum and Thrombopoietin on the Percentage of Small Acetylcholinesterase-positive Cells in Bone Marrow of Mice, Exp. Hematol, Nov. 1981, vol., 9, No. 10, pp. 1002–1010.

T. P. McDonald, Assay and Site of Production of Thrombopoietin, British Journal of Haematology, 1981, 49, pp. 493–499.

T. P. McDonald & R. K. Shadduck, Comparative Effects of Thrombopoietin and Colony-Stimulating Factors, Exp. Hematol, Jul. 1982, vol. 10, No. 6, pp. 544–550.

T. P. McDonald & G. D. Kalmaz, Effects of Thrombopoietin on the Number and Diameter of Marrow Megakaryocytes of Mice, Exp. Hematol, Feb. 1983, vol. 11, No. 2, pp. 91–97.

T. P. McDonald and G. D. Kalmaz[2], Nephrectomy Abolishes the Increase in Small Acetycholinesterase-Positive Immature Rat Megakaryocytes Induced by Acute Thrombocytopenial (41715), Proceedings of Soc. for Exp. Biology and Medicine 180, pp. 50–56 (1985).

T. P. McDonald, et al, Recovery of thrombopoietin During Purification, Biochemical Medicine and Metabolic Biology 37, 335–343, 91987).

Jane W. Ogle et al, The in Vitro Production of Erythropoietin and Thrombopoietin, Scand J Haematol (1978) 21, pp. 188–196.

T. P. McDonald, Thrombopoietin: Its History, Characterization and Future, University of Tennessee, College of Veterinary Medicine, Jul. 1, 1986.

G. D. Kalmaz and T. P. McDonald, Effect of Thrombopoietin on In Vitro Production of Megakaryocytes form Fetal Mouse Liver Cells (42142) Proceedings of the Society for Experimental Biology and Medicine, 180, pp. 50–56 (1985).

T. P. McDonald et al, Purification and Characterization of a Thrombocytopoiesis-Stimulating Factor from Human Embryonic Kidney Cell Cultures, 17th Annual Meeting-ISEH (1988).

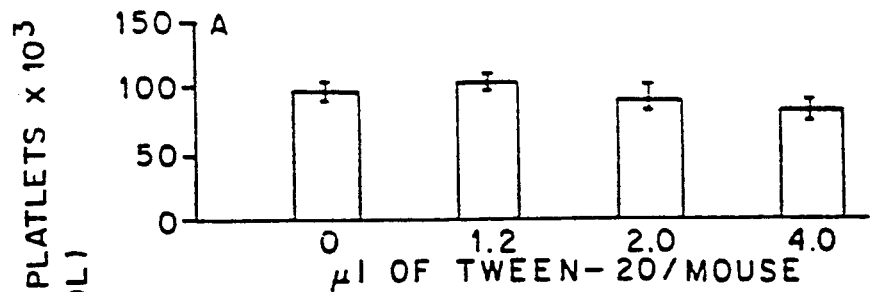
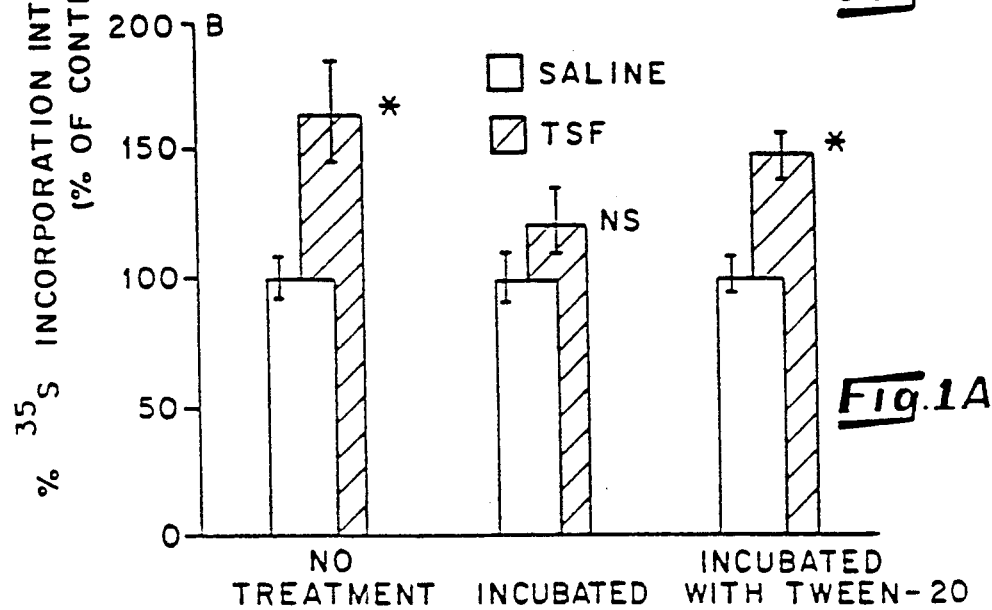
Fig. 1B
Fig. 1A
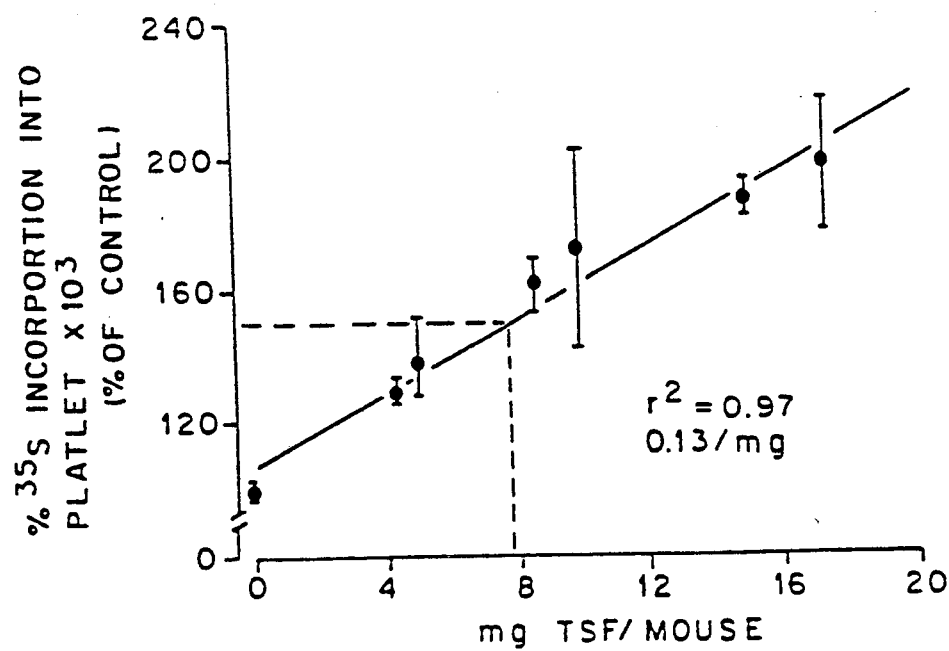
Fig. 2

POLYPEPTIDE AND A METHOD FOR ITS PRODUCTION

"This invention was made with government support under Grant No. RO1-HL-14637 from the National Institutes of Health. The government has certain rights in this invention."

The present invention relates to compounds having pharmacological activity and a method for producing the same.

The present invention resides in a new polypeptide and in a method for producing the same. The preferred method comprises chromatographing a crude compound-containing medium on a dextran derived chromatography column; precipitating the eluate in a water-ethanol solution; electrophoresing the precipitate in a polyacrylamide gel; and chromatographing the extract on a reverse phase - high performance liquid chromatography column.

The present compound is useful in stimulating thrombocytopoiesis.

The present polypeptide has a molecular weight of approximately 30,000 daltons which may be a dimer of two 15,000 dalton units. The compound has an isoelectric pH of about 4.47 and an activity of 21,000 to 117,000 units per mg of protein An activity unit for the compound is defined as the amount of material in a mg of protein that is required to increase the % $^{35}S$ incorporation into platelets of mice by 50% above base-line in an immunothrombocythemic assay and it is determined by dividing one milligram by the amount of protein (in milligrams) needed to increase the percent $^{35}S$ incorporation into platelets. This may be compared to prior art which discloses thrombocytopoiesis stimulating compounds with molecular weights of 32,000 daltons, an isoelectric pH of 4.7, and an activity of no more than 11,000 units per mg of protein.

The present invention also relates to a method for the production of the compound that provides for a relatively rapid method of production of the new polypeptide. Also the method as recited in the claims allows the polypeptide to be stored, without losing its activity, for several days.

FIG. 1A represents the effects of Tween-20 on %$^{35}S$ incorporation into platelets of mice in an immunothrombocythemic mice.

FIG. 1B shows the effects of Tween-20 on the stability of the present polypeptide.

FIG. 2 shows the dose-response relationship between the amount of crude medium in mg of polypeptide and the %$^{35}S$ incorporation into platelets of mice in an immunothrombocythemic assay.

Figure 5:
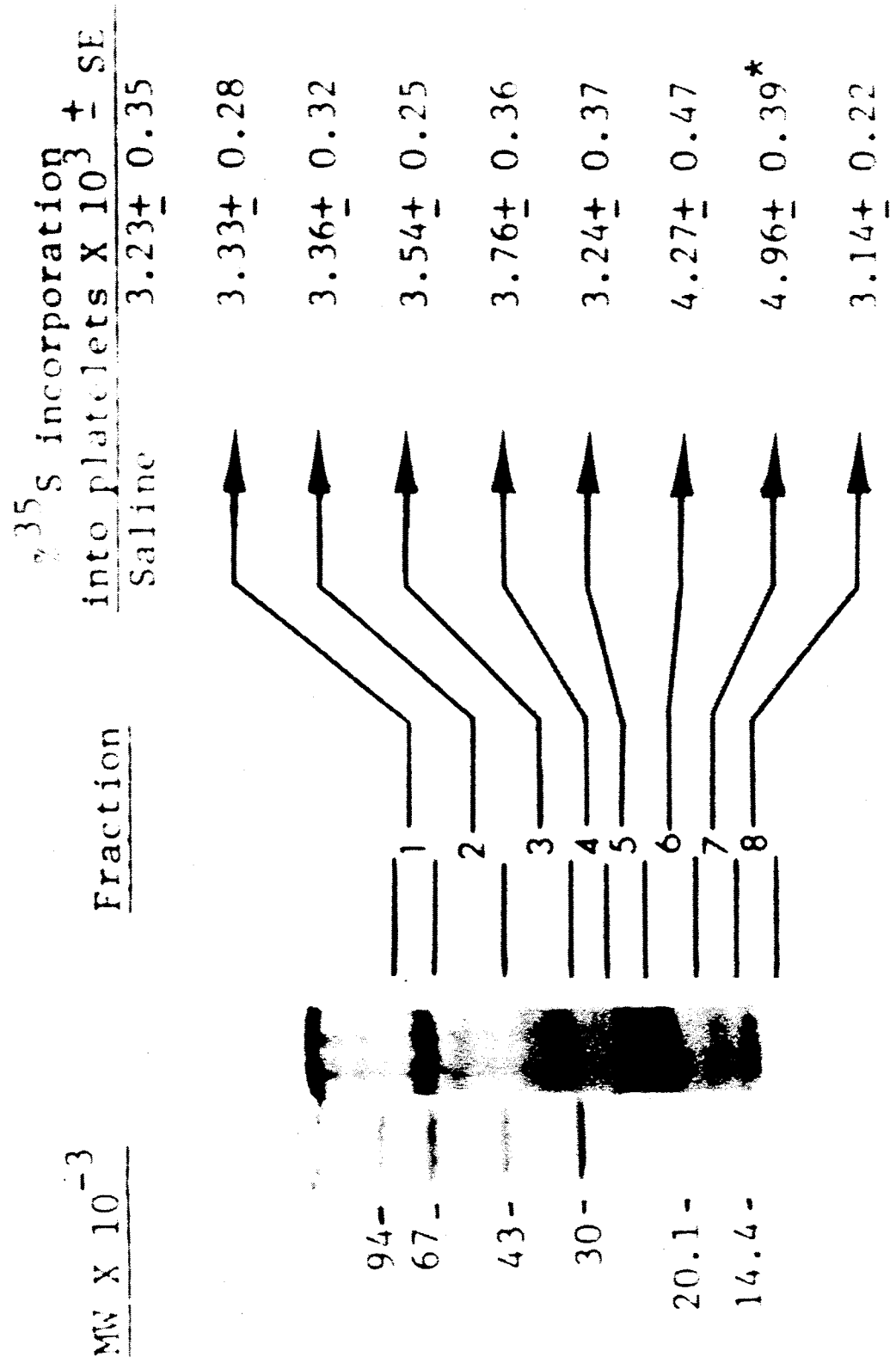
FIG. 5 shows the results of SDS-PAGE of post-ethanol prepared polypeptide.
Figure 11A:
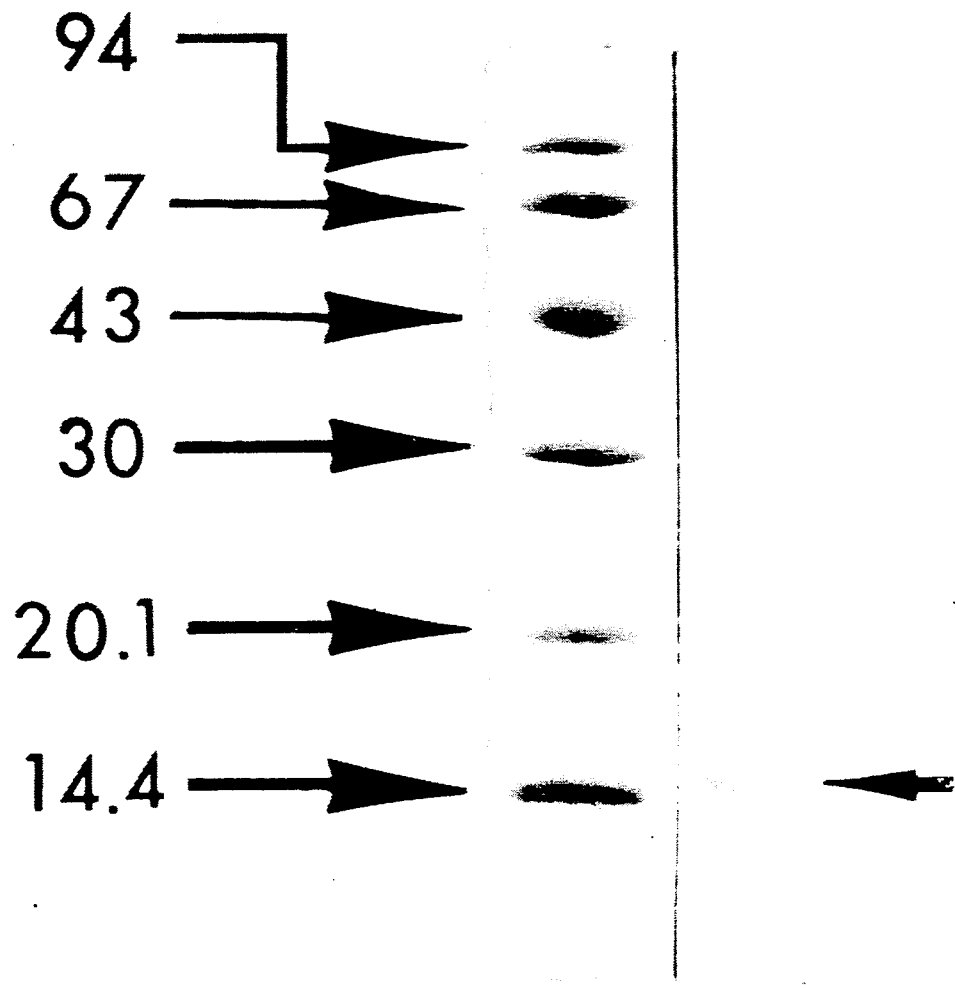
Figure 11B:
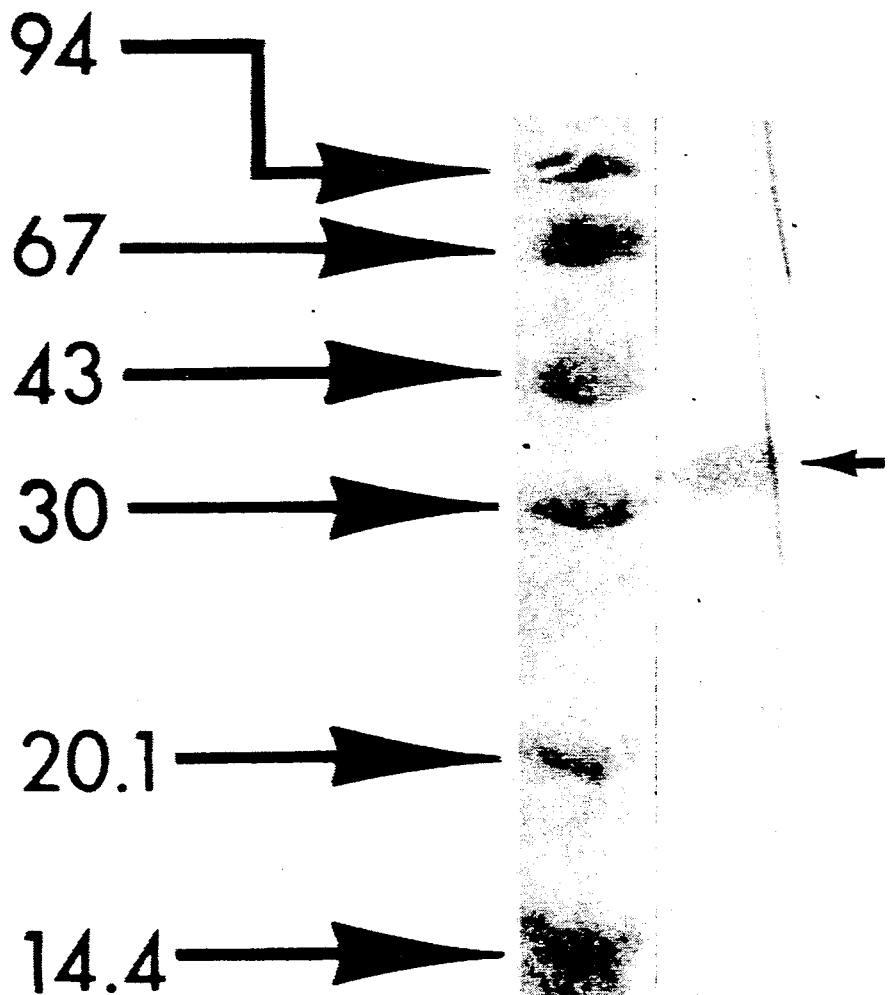

FIGS. 11A and B show the results of SDS-PAGE of Step III, Fraction 7 (presented in FIG. 5). In FIG. 11A, the gel on the left shows the MW standards and the gel on the right shows the results of electrophoresing the post SDS-PAGE polypeptide-rich material after heating 10 min. at 100° C. in denaturing conditions. In FIG. 11B the polypeptide was dialyzed in a weak phosphate buffer, freeze-dried, and applied to the gel without heating using non-denaturing conditions. These figures show that a 15 Kd MW polypeptide will self-associate under non-denaturing conditions, leading to polypeptide with a molecular weight of about 30 Kd.

In order to facilitate a further understanding of the invention, the following examples are given primarily for purposes of illustrating certain more specific details thereof.

EXAMPLE 1

Sephadex Column Chromatography

Crude polypeptide from human embryonic kidney culture media was chromatographed on a 4.4×90 cm column of a bead-formed, cross-linked dextran gel (SEPHADEX G-75, Pharmacia, Upsala, Sweden) using as an eluting buffer 2.5 mM $NaH_2PO_4$- $Na_2HPO_4$ in 75 mM NaCl, pH 7.0 at 4°. The maximum protein that could be applied to the column at each time was 1 gram; therefore, for this work each lot of polypeptide was the result of 12 grams of polypeptide enriched eluate prepared in 12 weekly runs on columns. The column eluate was monitored at 280 nm and tubes containing the protein within each run were pooled into fractions Fractions of approximately 160 ml each were collected and concentrated on an Amicon TCF-10 with YM10 membranes, lyophilized to dryness, and stored at −76°.

Ethanol Precipitation

The post-Sephadex polypeptide enriched eluates were further purified by ethanol precipitation. Proteins were precipitated at 0-40, 40-60, and 60-80% ethanol concentrations and sedimented by centrifugation (25,700×g) at 4° C. The precipitates were lyophilized to dryness and stored at −76° C. Before reconstituting, 0.5 ml of 5% Polyoxyethylene-Sorbitan Monolaurate (TWEEN-31 -b 20, Sigma, St. Louis, Mo.) was added to enhance polypeptide stability.

Sodium Dodecylsulfate - Polyacrylamide Gel Electrophoresis (SDS - PAGE)

Concentrated post-ethanol precipitate (approximately 2 mg/100 μl ) was mixed with a protein solvent solution containing EDTA, Tris-HCl, SDS, B-mercaptoethanol, bromophenol blue, sucrose. The precipitated specimens were applied to 1.4×11 cm tubes containing 10% acrylamide gel and were electrophoresed for about 8 hours at 60 mA. For each run, one tube containing the polypeptide enriched precipitate and another tube containing the MW standards were stained with Coomassie brilliant blue. The remaining gels were cut into pieces that contained protein bands identified by the stained gel and the protein was extracted from the gels by homogenization and washing 3 times with distilled water. The extracted protein was lyophilized to dryness and stored at −76° C.

Reverse Phase - High Performance Liquid Chromatography

Reverse phase-high performance liquid chromatography (RP-HPLC) was performed using a 4.6×30 mm 300A pore size, 7 μm particle size column model CO3-GU, RP-300, C8 form BROWNLEE Labs, Santa Clara, Calif). The A buffer was 0.01 M $NaH_2PO_4$, pH 6.65. The B buffer was a 20% solution of the A buffer in acetonitrile. The instrument was a Beckman HPLC system and a flow rate of 200 μl per minute and was used at room temperature. Each fraction was the result of a 9 minute collection time. All mobile phases were prefiltered (0.22 m, Millipore) and degassed in vacuo, aided by brief sonication. After RP-HPLC, the fractions were dialyzed using 1000 MW cutoff membranes against distilled water, lyophilized to dryness, and reconstituted into saline.

The polypeptide produced had a molecular weight of 30,000 daltons, an isoelectric pH of 4.47, and an activity of 21,000 units per mg. of protein.

TABLE I

Table I presents the purification factors of the present polypeptide from kidney cell culture using the present procedure.

with the present method, the compound has greater activity and a longer active life than thrombocytopoiesis stimulating compounds of the prior art.

Stability Studies

FIGS. 1A and 1B show the results of testing the effects of Tween-20 on $\%^{35}S$ incorporation into platelets of assay mice (FIG. 1A) and the effects of Tween-20 in protecting the biological activity of the present polypeptide (FIG. 1B) during incubation at room temperature. The results indicate that TWEEN-20 by itself did not stimulate $^{35}S$ incorporation into platelets of assay mice. Moreover, Tween-20 protected the biological activity of the polypeptide (FIG. 1B) during prolonged incubation. In the studies outlined herein, TWEEN-20 was added to the preparations before storage in an effort to retain greater amounts of the biological activity.

Each bar is the average of 5 mice and the vertical bars represent the SE. *Significantly greater than suitable control, P <0.05; NS indicates not significantly different from control. Incubation was at 22° C. for 48 hours; in FIG. 1B, Tween-20 was added to the polypeptide-rich preparation before incubation at the rate of 2 l/mouse.

Purification of Polypeptide

FIG. 2 illustrates the results of determining, in a dose-response experiment, the potency of crude polypeptide-rich kidney cell culture medium. As shown, a linear correlation ($r^2=0.97$) over a broad dose range was observed (P<0.0005) with 0.13 unit of polypeptide per mg of protein.

Figure 3A:
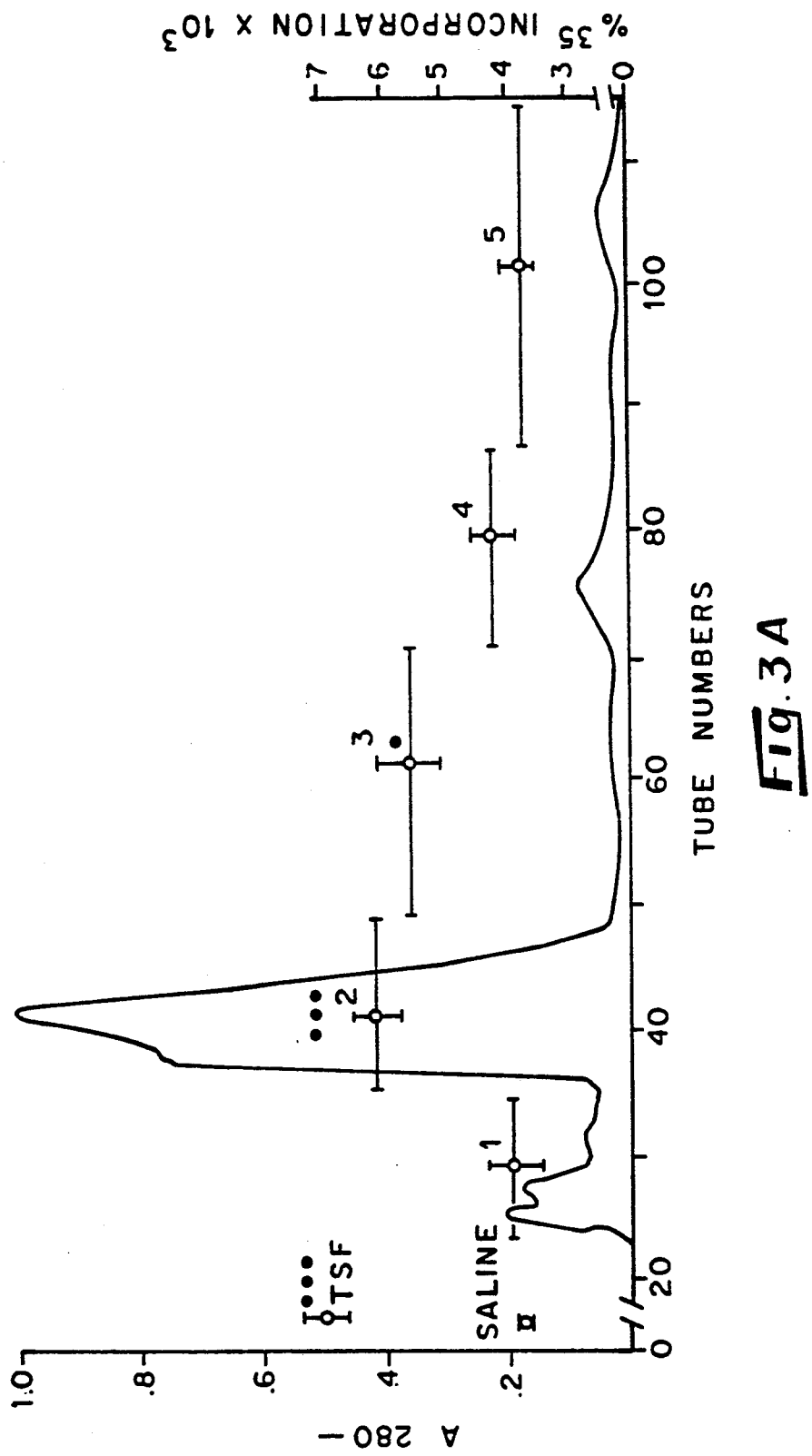
FIG. 3A shows a dose-response experiment of Fraction 3 of FIG. 3.
Figure 3B:
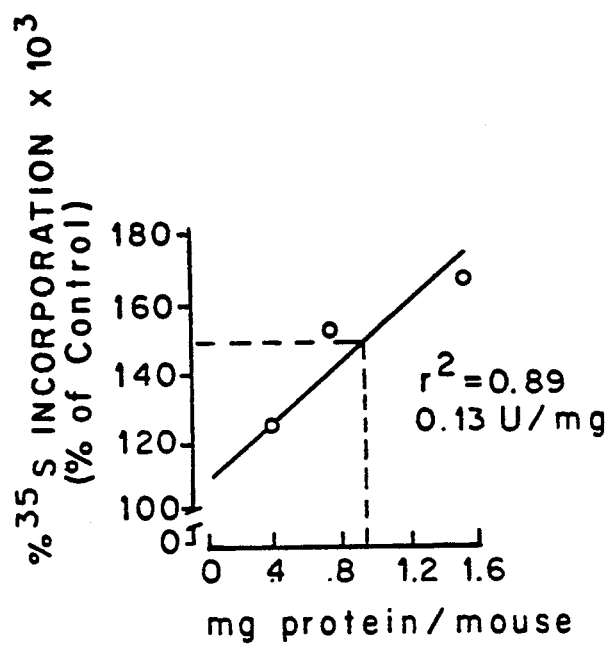
FIG. 3 shows the purification of crude polypeptide by Sephadex G-75 column chromatography.

The crude polypeptide preparation was subjected to partial purification by SEPHADEX G-75 column chromatography (Step I). FIG. 3A shows the protein elution pattern; contents of collection tubes were pooled into 5 fractions (as indicated) and the fractions were tested in

TABLE I

| | | Purification Factors from Kidney Cell Culture Medium | | | | | | | |
|---|---|---|---|---|---|---|---|---|---|
| | | Protein (mg) | | | Polypeptide Units | | | Purification | Specific Activity |
| Step | Method | Starting | Recovery | % | Starting | Recovery | % | Factors | (units/mg Protein) |
| Crude | Culture Media | — | — | — | — | — | — | 0 | 0.13 |
| I | Sephadex | $6 \times 10^4$ | 2175 | 3.6 | $16.8 \times 10^3$ | 2240 | 13 | 8 | 1.03 |
| II | Ethanol | 2070 | 262 | 12.7 | 2130 | 845 | 40 | 25 | 3.23 |
| III | SDS-PAGE | 255 | 10 | 3.9 | 825 | 196 | 24 | 150 | 19.6 |
| $IV_a$ | RP-HPLC | 6.6 | $6.6 \times 10^{-3}$ | 0.1 | 130 | 58 | 45 | 68,000 | 8800 |
| $IV_b$ | RP-HPLC | 5.9 | $4.7 \times 10^{-3}$ | 0.08 | 135 | 100 | 74 | 160,000 | 21000 |

EXAMPLE 2

The same conditions as Example 1 were used except that, prior to applying the precipitate specimens to the tubes of acrylamide gel, the specimens were boiled for ten minutes.

The product had a molecular weight of 15,000 daltons, an isoelectric pH of about 4.47, and an activity of at least 21,000 units per mg of protein. When processed under nondenaturing conditions, the product self-associates to form a polypeptide with a molecular weight of 30,000 daltons.

From the foregoing, it may be seen that the new polypeptide produced has a molecular weight of 15,000 in its monomeric forms and 30,000 daltons as a dimer, an isoelectric pH of 4.47, and an activity of at least 21,000 units per mg of protein. Also, the method as disclosed provides a relatively rapid method of production of the compound. Additionally, as produced in accordance the mouse bioassay for polypeptide. In FIG. 3A, the solid line represents the protein elution pattern at A (AUFS=1.0); each fraction was concentrated on a high performance filtration system with membranes which will filter material with molecular weights of <10,000 (model TCF-10 with YM10 membranes from Amicon Corporation, Danvers, Mass.), lyophilized, and reconstituted into saline to 12.5 ml; each assay mouse was injected with 0.05 ml of this preparation diluted into 2.0 ml of saline. Open circles represent the polypeptide content of each fraction (shown by horizontal bars), saline and polypeptide starting material The amount of protein injected into each mouse was: F1, 1.1 mg; F2, 5.5 mg; F3, 0.69; F4, 0.042 mg; and F5, 0.019 mg. Vertical bars represent SE and each point is the average of 5 mice. Values were significantly elevated over saline-control; *P<0.05, ***P<0.0005. As shown, Fractions 2 (the major protein peak) and 3 (area of low protein content following the major protein peak) contained almost all of the polypeptide. This work demonstrates that 13% of the polypeptide that was applied to the column was recovered in Fraction 3, but only 3.6% of the protein was recovered, indicating that, by this technique, a significant purification of polypeptide was achieved (8-fold). This finding indicates that the MW of the polypeptide in non-denaturing reagents is between 30 and 50 K daltons (d). Also shown in FIG. 3A is a dose-response experiment using Fraction 3. The specific activity of this preparation was found to be 1.03 U/mg protein ($r^2=0.89$, $P<0.005$). A summary of these data is presented in Table 1.

Figure 4A:
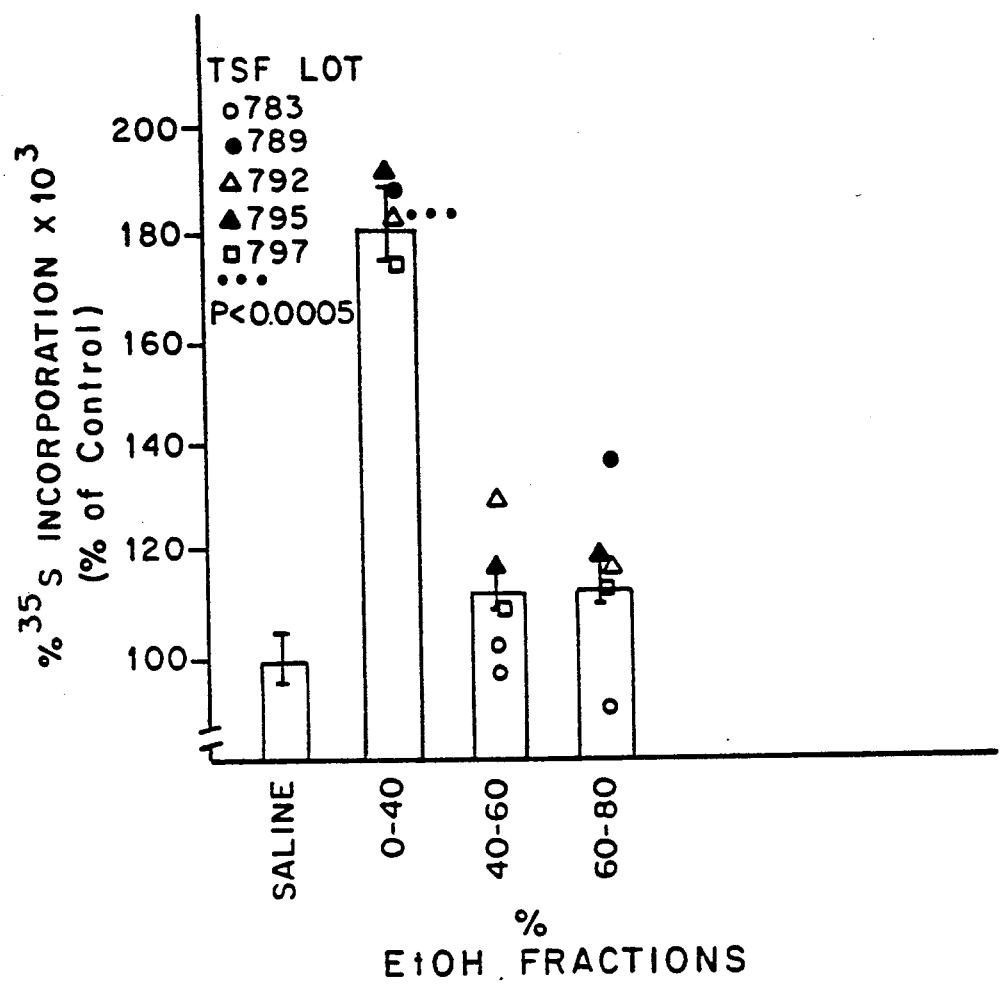
FIG. 4 shows further purification of post-Sephadex polypeptide by ethanol precipitation.
FIG. 4B shows a dose-response procedure of fraction 0-40% of one of the lots of FIG. 4A.
Figure 4B:
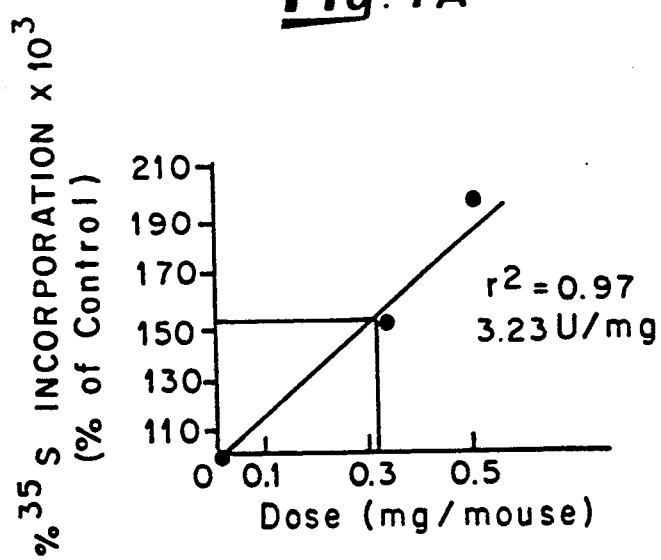

FIG. 4 depicts the results of subjecting post-Sephadex G-75 Fraction 3 material to ethanol precipitation. Proteins that precipitated at 0–40, 40–60, and 60–80% ethanol concentrations were collected at 4° C. The precipitated materials were freeze-dried, stored at $-76°$ C., and resuspended into 10 ml of water containing 0.5 ml of 5% TWEEN-20. Reconstituted fractions were tested in the immunothrombocythemic mouse assay. Bars represent the average of 5 separate experiments (Lots) using 12 grams of crude starting material for each Lot. Vertical lines represent the SE, ***$P<0.0005$. As shown, in five separate experiments the polypeptide activity was localized in the 0–40% ethanol fraction, as indicated by a highly significant ($P<0.0005$) increase in %$^{35}$S incorporation into platelets of assay mice (average 182% of saline-control values). Proteins precipitated at 40–60% and 60–80% ethanol concentrations did not contain significant polypeptide activity when tested in the mouse bioassay. FIG. 4B shows a dose-response relationship between the amounts of polypeptide-rich material precipitated at 0–40% ethanol concentration and %$^{35}$S incorporation into platelets of assay mice ($r^2=0/97$, $P<0.0005$). This step represents a further 3-fold purification of polypeptide or a purification factor of 25 from the starting material (Table 1).

Figure 6:
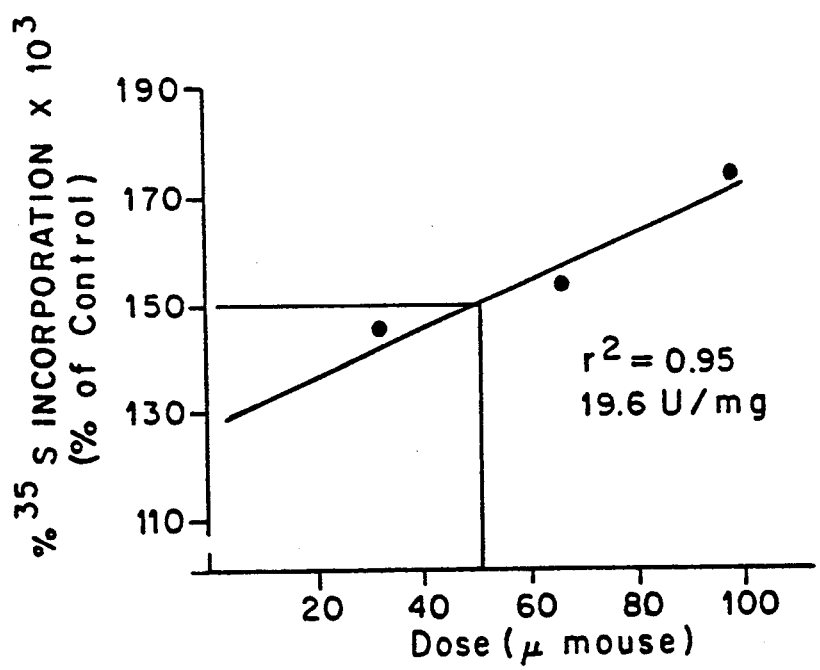
FIG. 6 shows a dose-response procedure between the amounts of SDS-PAGE, Fraction 7 TSF-rich material prepared in FIG. 5 and the %$^{35}S$ incorporation into platelets of assay mice.

FIG. 5 shows the results of subjecting the 0–40% ethanol fraction to preparative SDS-PAGE. The gel on the left contains the MW standards and the gel on the right shows the results of electrophoresing 2.21 milligrams of the 0–40% ethanol polypeptide-rich protein in each tube. The gels were cut as indicated, and the proteins were extracted and assayed in the bioassay for polypeptide, 5 mice/group. Only Fraction 7 ($-15$ Kd MW material) stimulated platelet production in the mouse (*$P<0.025$). As illustrated, several different classes of proteins were still present in the 0–40% ethanol; fraction after staining with Coomassie blue, but only Fraction 77 (MW of about 15 Kd) contained significant amounts of polypeptide ($P<0.025$). In FIG. 6, a dose-response relationship of Step III, Fraction 7 polypeptide is shown (Table 1). A highly significant dose-response relationship ($r^2=0.95$, $P<0.0005$) with 19.6 U/mg of protein was found. This step represents a further 6-fold purification or about 150-fold purification over the starting material (Table 1).

Figure 7:
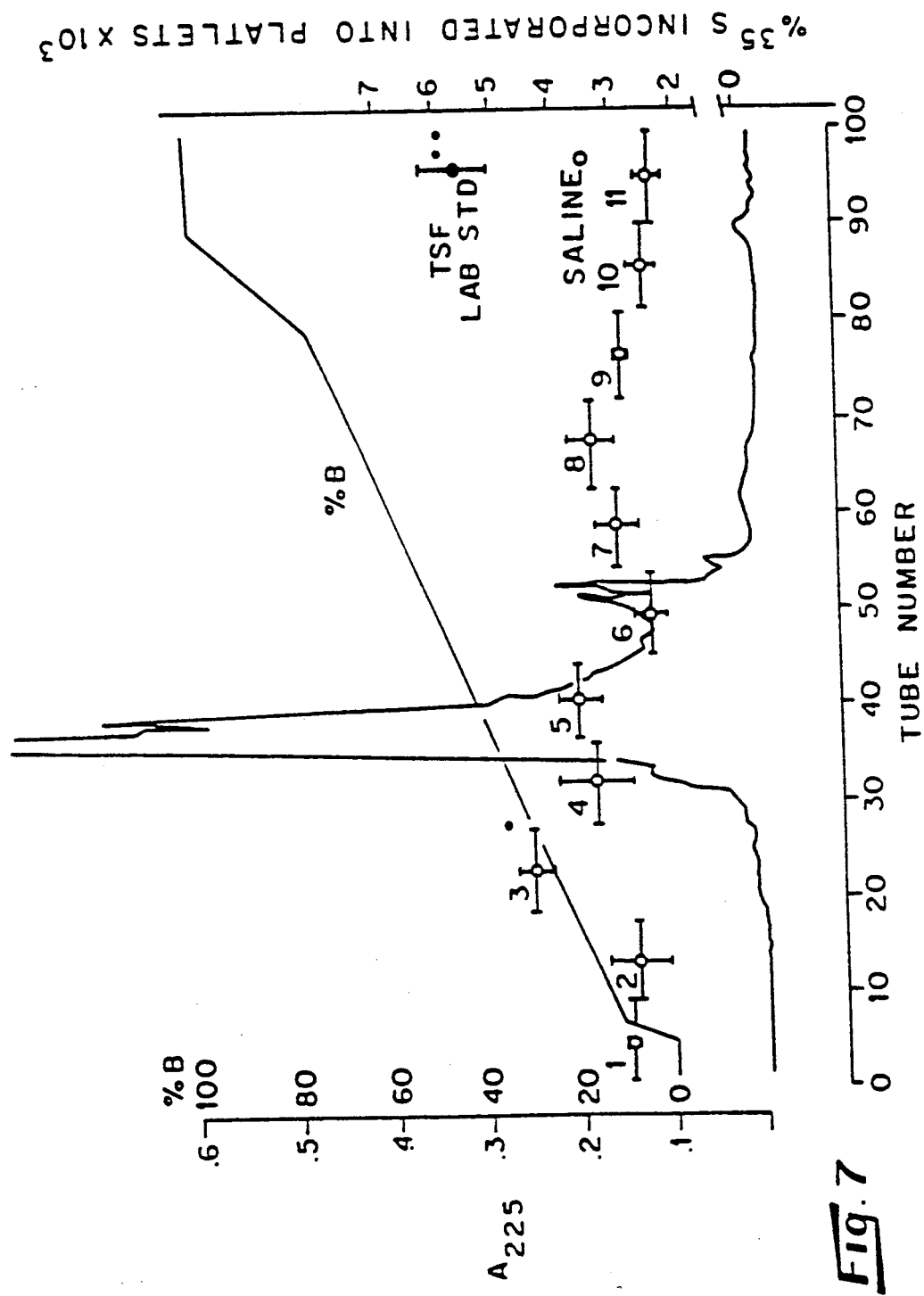
FIG. 7 shows a RP-HPLC of post-SDS-PAGE polypeptide-rich material.

The post-SDS-PAGE material was then subjected to RP-HPLC. As illustrated in FIG. 7, polypeptide was found in an area of low protein content that eluted from the column before the major protein peak, i.e., Fraction 3 ($P<0.01$). All other fractions gave %$^{35}$S incorporation into platelet values that were not significantly elevated over the values obtained by saline-treatment. The column was a BROWNLEE CO-b 3-1 -GU,C8 $4.6\times30$ mm; buffer A was 0.01 M NaH PO , pH 6.7; buffer B was 20% buffer A in $CH_3CN$; flow rate was 200 μl/min. at 22° C. A Beckman HPLC system was used. Each fraction was collected for 9 minutes, the material was dialyzed against distilled water using 1000 MW cutoff membranes, lyophilized to dryness, and resuspended into saline for testing in the immunothrombocythemic mouse assay Open circles represent the polypeptide content of each fraction (shown by horizontal bars) and saline; the closed circle represents the polypeptide content of the starting material. Vertical bars represent the SE *$P<0.01$, **$P<0.005$. Dose-response experiments indicated that this product had a specific activity; of $\sim 8,800$ U/mg of protein, representing a purification factor of $\sim 68,000$ over the starting material (Table I, Step IVa).

Figure 8:
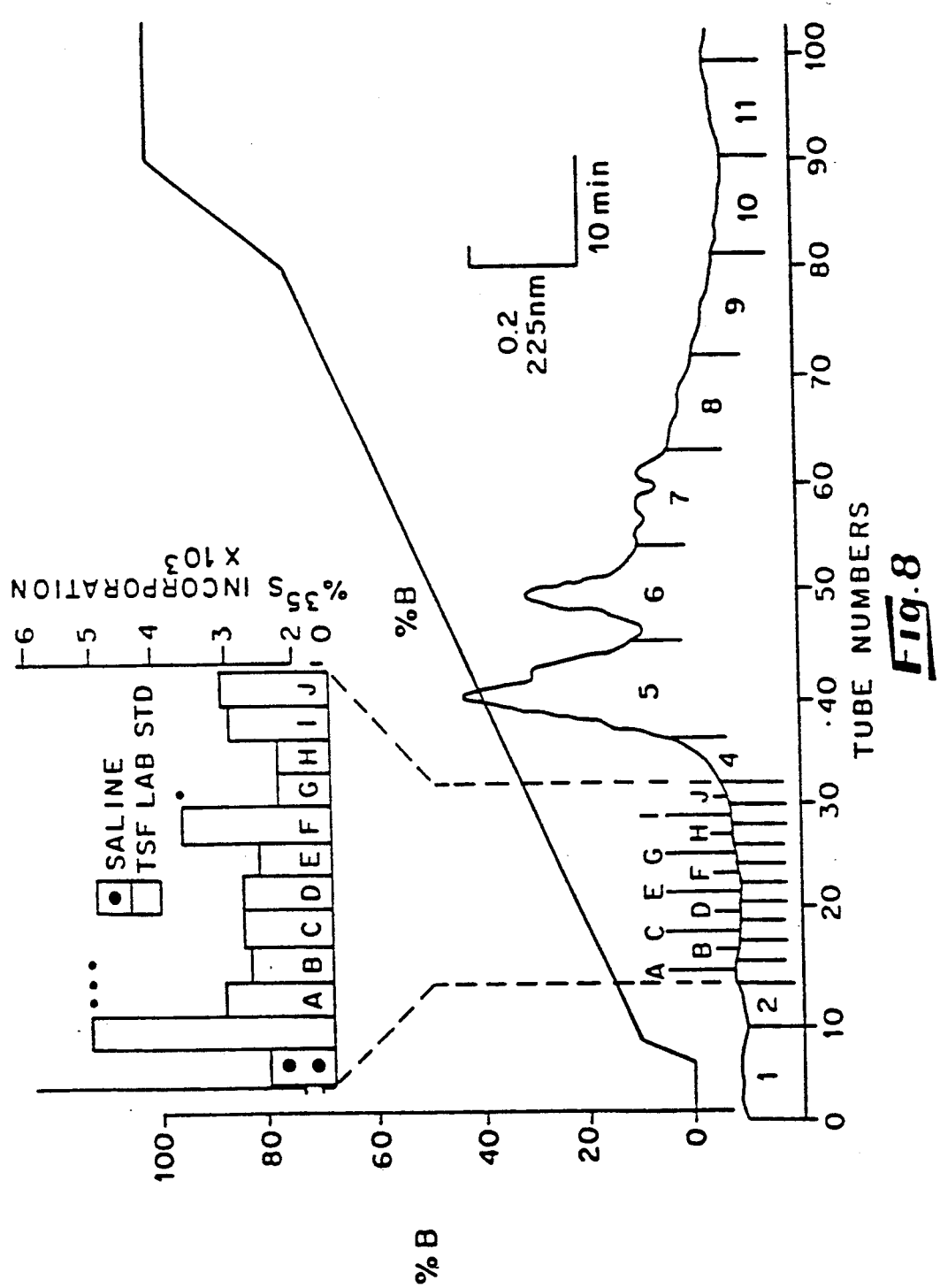
FIG. 8 shows a RP-HPLC of another batch of the same material as presented in FIG. 7 using the same column techniques, except the polypeptide active region (tubes 15-35) was subdivided into 10 groups, dialyzed against water, freeze-dried, and assayed in the mouse bioassay for the polypeptide, *$P<0.025$, ***$P<0.00005$.

FIG. 8 shows the results of another experiment in which the post-SDS-PAGE polypeptide was subjected to RP-HPLC. In this experiment the area that was shown to have significant bioactivity in the previous study (FIG. 7) was further subdivided into 10 fractions and tested in the mouse assay for polypeptide One of the subfractions (Fraction F) contained significant polypeptide bioactivity ($P<0.025$). This material was highly potent, about 21,000 U/mg protein (Table 1, Step IVb) and represents a purification factor of about 164,000-fold.

Figure 9:
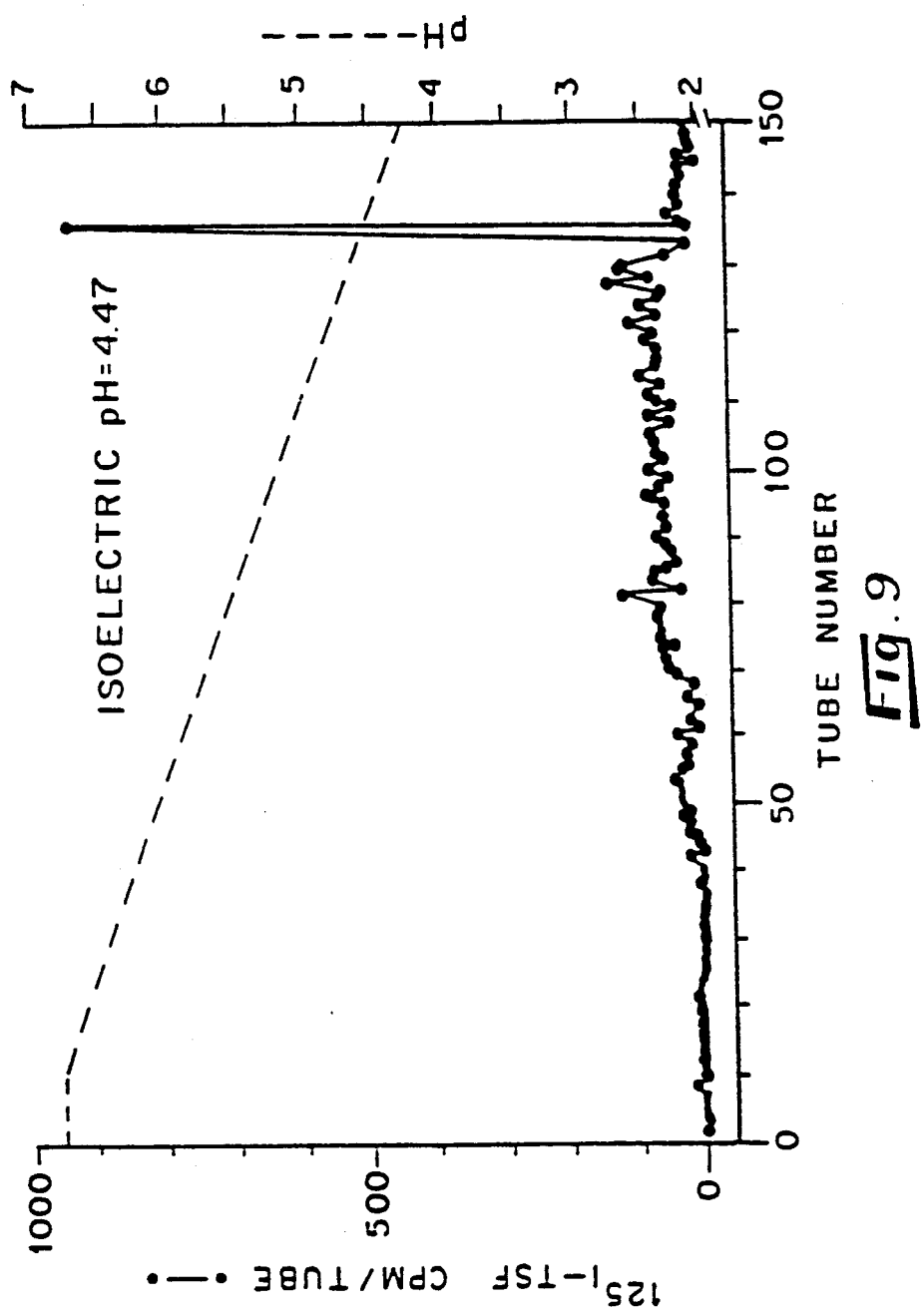
FIG. 9 shows the chromatofocusing of $^{125}I$-polypeptide (step IVb, Fraction 3F) from the procedure presented in FIG. 8.
Figure 10:
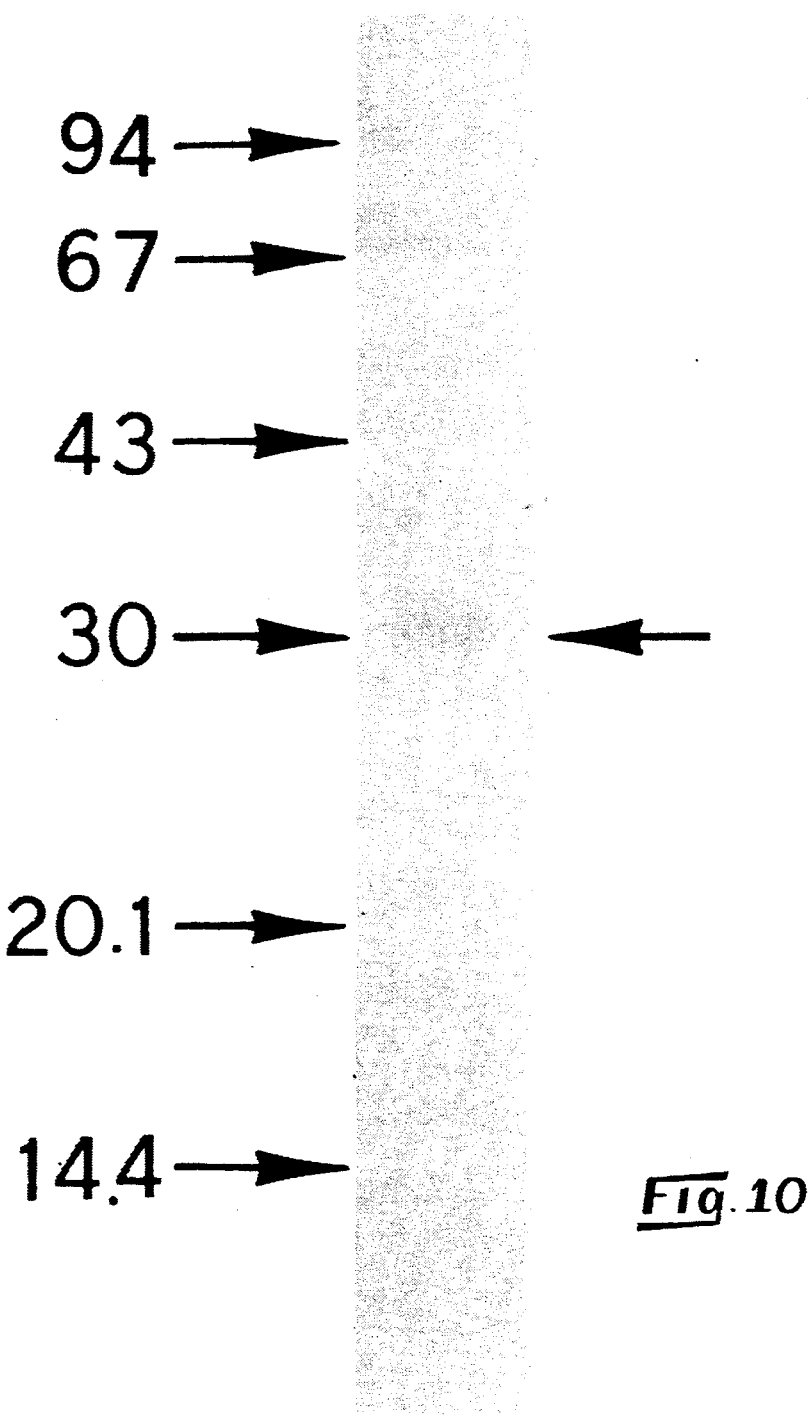
FIG. 10 shows an autoradiograph of SDS-PAGE of $^{125}I$-polypeptide used in FIG. 9 (Step IVb, Fraction 3F).

The highly purified polypeptide (Step IVb, Fraction 3F) was iodinated and subjected to chromatofocusing using a gradient of a buffer solution between 7 and 4 (POLYBUFFER 74, Pharmacia, Upasla, Sweden) and imidazole-HCl. The elution pattern of $^{125}$I-TSF from the column showed a single, sharp band of isoelectric pH 4.47, with a peak width of 0.01 pH units (FIG. 9). FIG. 10 shows the results of applying the $^{125}$I-TSF to vertical slab-SDS-PAGE in non-denaturing buffers, staining with silver, and exposing the gel to film for an autoradiograph Although no visible bands were present with silver staining, the autoradiograph showed a single band with a MW of 30 Kd. The $^{125}$I polypeptide appears to be homogeneous as judged by both chromatofocusing and autoradiography of SDS-PAGE.

Molecular Weight Determination of TSF

FIG. 11 shows the results of subjecting the polypeptide-rich post-SDS-PAGE material (Step III, Fraction 7) to additional electrophoresis after dialysis and lyophilization using both denaturing and nondenaturing conditions. As shown in FIG. 11A, after electrophoresis in denaturing buffers and staining with Coomassie blue there Was a single protein band at 15 Kd. FIG. 11B shows the same material that was used in FIG. 11A, but the protein was dialyzed in a weak phosphate buffer, lyophilized and subjected to SDS-PAGE without boiling or the use of strong denaturing conditions. As shown, materials that were previously shown to migrate at $\sim 15$ Kd MW were found to electrophorese to $\sim 30$ Kd MW. This finding leads to the conclusion that the present polypeptide has the ability to self-associate in non-denaturing conditions and exist as a dimer.

In the precent invention a four-step procedure is used, consisting of SEPHADEX column chromatography, ethanol precipitation, SDS-PAGE, and RP-HPLC for the purification of the polypeptide. With the aid of TWEEN-20, the final product maintained its biological activity for several weeks at $-76°$ C. The purified polypeptide was very potent (21,000 U/mg protein) and migrated on SDS-PAGE and chromatofocused as a homogeneous product.

TWEEN-20 aided significantly in maintaining the biological activity of polypeptide. The data (FIG. 1) showed that TWEEN-20, without altering platelet production itself, protected the polypeptide from denaturation and helped in maintaining its biological activity after long periods of incubation at room temperature.

In the present invention it has been found that by using partially purified polypeptide-rich preparations, significant amounts of polypeptide were precipitated with ethanol concentrations of 0–40% (FIG. 4) as compared to the use of 40% or greater ethanol concentrations. It appears that during the purification of polypeptide in accordance with the present disclosure, chemicals were removed that significantly affected the precipitation characteristics by ethanol. Further, in the present invention, the method used was particularly successful in removing albumin from polypeptide. It is postulated that partial separation of albumin from the polypeptide moiety may have influenced the hydrophobic interactions of organic solvents to the polypeptide, leading to the requirement for different percentages of ethanol for its precipitation. In any event, the data show quite clearly that partially purified polypeptide, prepared by SEPHADEX chromatography, precipitates at 0–40% ethanol concentrations.

The purified polypeptide of the present work was highly active. It should be noted that TWEEN-20 was used to protect the molecule from denaturation. The use of this protection agent allowed the use of drastic purification procedures, to include RP-HPLC with acetonitrile buffers and heating the protein to 100° C. for 10 minutes prior to placing it on polyacrylamide gels. These procedures appear to be necessary for the separation of polypeptide from albumin, leading to a purified preparation suitable for amino acid sequencing. The results indicate that these procedures, in the presence of TWEEN-20, released the polypeptide molecule free of albumin in a stable, purified moiety.

The polypeptide produced by the disclosed method showed an isoelectric pH of 4.47 (FIG. 9). The purified material was well-focused with a single, sharp peak and appeared to be a homogeneous protein (FIG. 10).

As shown herein, the MW of the polypeptide varied depending upon the method of separation that was used for its preparation Boiling the preparations for 10 minutes in the presence of denaturing reagents, before applying to SDS-PAGE, yields a 15 Kd protein band that contains most of the polypeptide bioactivity (FIGS. 5 & 6). However, if the 15 Kd MW polypeptide (FIG. 11A) is processed in non-denaturing conditions, it was shown to self-associate to yield a ~30 Kd MW protein (FIG. 11B).

What is claimed is:

1. A purified polypeptide useful in stimulating thrombocytopoiesis wherein said polypeptide:

has a specific activity at least 160,000 times greater than the unpurified polypeptide in a human embryonic kidney cell culture containing the unpurified polypeptide;

has a molecular weight, as determined by sodium dodecyl sulfate polyacrylamide gel electrophoresis under reducing conditions, of about 15,000 daltons as a monomer;

is stained by Coomassie blue;

has an isoelectric pH of about 4.47; and has a specific activity of at least 21,000 units per milligram of said polypeptide where a unit of specific activity is determined by dividing one milligram by the weight of said polypeptide required to increase the percent $^{35}S$ incorporation into platelets of mice by 50 percent above baseline in an immunothrombocythemic assay.

* * * * *